US012629024B2

(12) United States Patent
Künzi et al.

(10) Patent No.: US 12,629,024 B2
(45) Date of Patent: May 19, 2026

(54) MULTI-MODAL RETINAL IMAGING PLATFORM

(71) Applicant: ECOLE POLYTECHNIQUE FEDERALE DE LAUSANNE (EPFL), Lausanne (CH)

(72) Inventors: Matthieu Künzi, Geneva (CH); Timothé Laforest, Crozet (FR); Christophe Moser, Lausanne (CH)

(73) Assignee: ECOLE POLYTECHNIQUE FEDERALE DE LAUSANNE (EPFL), Lausanne (CH)

( * ) Notice: Subject to any disclaimer, the term of this patent is extended or adjusted under 35 U.S.C. 154(b) by 626 days.

(21) Appl. No.: 17/914,692

(22) PCT Filed: Mar. 25, 2021

(86) PCT No.: PCT/EP2021/057680
§ 371 (c)(1),
(2) Date: Sep. 26, 2022

(87) PCT Pub. No.: WO2021/191331
PCT Pub. Date: Sep. 30, 2021

(65) Prior Publication Data
US 2023/0346215 A1 Nov. 2, 2023

(30) Foreign Application Priority Data

Mar. 27, 2020 (EP) ..................................... 20166482

(51) Int. Cl.
*A61B 3/12* (2006.01)
*A61B 3/00* (2006.01)
(Continued)

(52) U.S. Cl.
CPC .......... *A61B 3/1233* (2013.01); *A61B 3/0008* (2013.01); *A61B 3/1015* (2013.01); *A61B 3/102* (2013.01); *G06T 7/50* (2017.01)

(58) Field of Classification Search
CPC ... A61B 3/1233; A61B 3/0008; A61B 3/1015; A61B 3/102; A61B 3/1225; A61B 3/1241; G06T 7/50
(Continued)

(56) References Cited

U.S. PATENT DOCUMENTS

2014/0055745 A1* 2/2014 Sato ....................... A61B 3/102
351/246
2015/0250383 A1 9/2015 Ribaric et al.
(Continued)

FOREIGN PATENT DOCUMENTS

JP 2020-6234 1/2020
WO 2009/098516 8/2009
(Continued)

OTHER PUBLICATIONS

International Search Report date Jun. 25, 2021, for PCT/EP2021/057680, 4 pp.
(Continued)

*Primary Examiner* — Mohammed A Hasan
(74) *Attorney, Agent, or Firm* — Nixon & Vanderhye PC

(57) ABSTRACT

The invention relates to oblique transscleral illumination of an eye fundus with at least one physical point light source around the eye allowing for dark field imaging combined with optical coherence tomography imaging.

15 Claims, 7 Drawing Sheets

(51) Int. Cl.
   *A61B 3/10* (2006.01)
   *G06T 7/50* (2017.01)
(58) Field of Classification Search
   USPC .......................................................... 351/206
   See application file for complete search history.

(56) References Cited

U.S. PATENT DOCUMENTS

| | | | |
|---|---|---|---|
| 2016/0270656 A1* | 9/2016 | Samec ................. | A61B 3/1035 |
| 2017/0172691 A1* | 6/2017 | Ulinskas .............. | A61B 3/0075 |
| 2021/0038071 A1* | 2/2021 | Tatara .................... | A61B 3/102 |
| 2021/0204809 A1* | 7/2021 | Hirose .................... | A61B 3/12 |

FOREIGN PATENT DOCUMENTS

| | | | |
|---|---|---|---|
| WO | 2017/195163 | 11/2017 | |
| WO | WO-2017195163 A1 * | 11/2017 | ........... A61B 3/0008 |

OTHER PUBLICATIONS

Written Opinion of the ISA date Jun. 25, 2021, for PCT/EP2021/057680, 6 pp.

* cited by examiner

FIG: 1
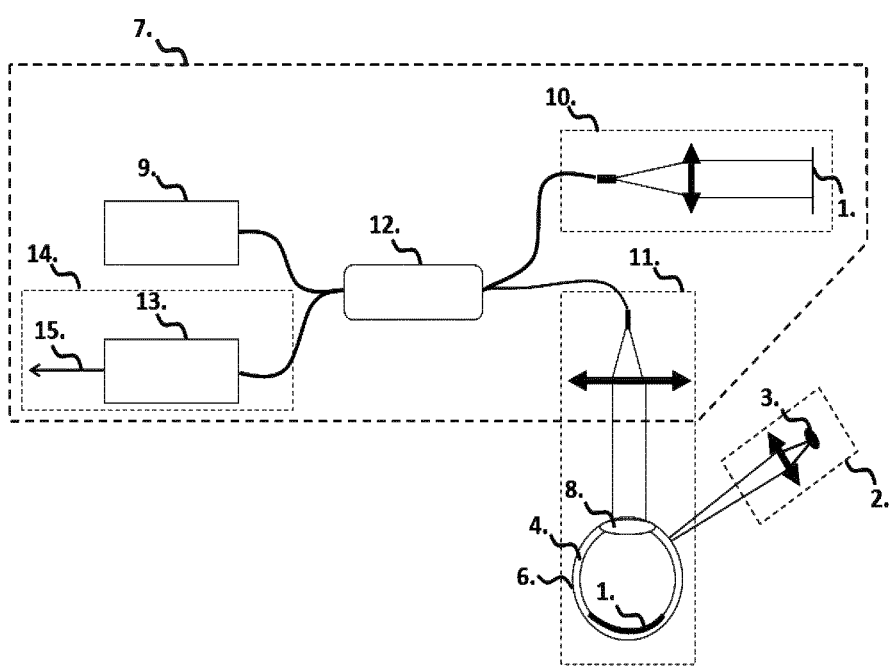
FIG: 2
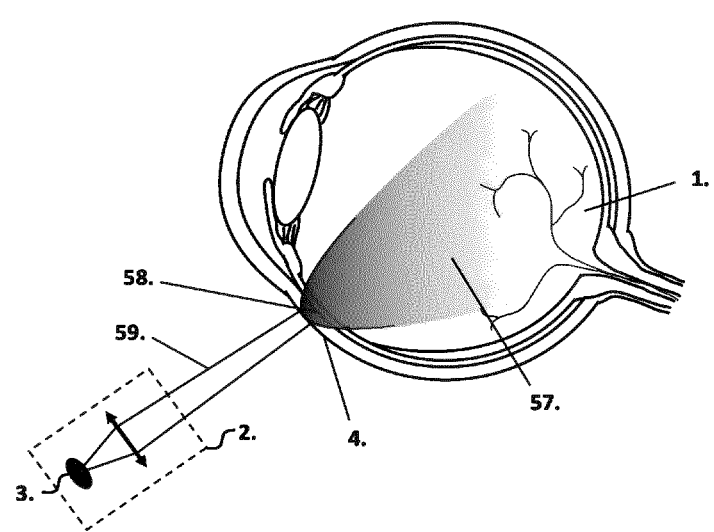

FIG: 3
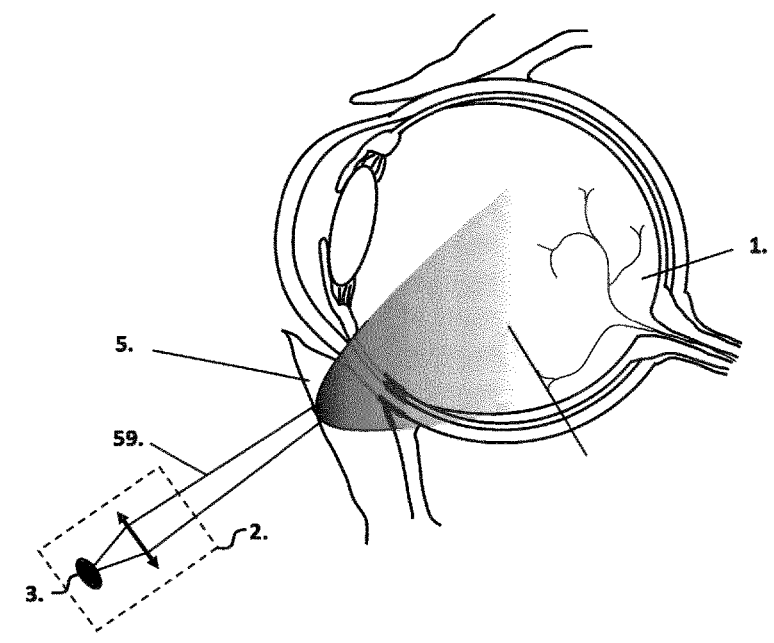
FIG: 4
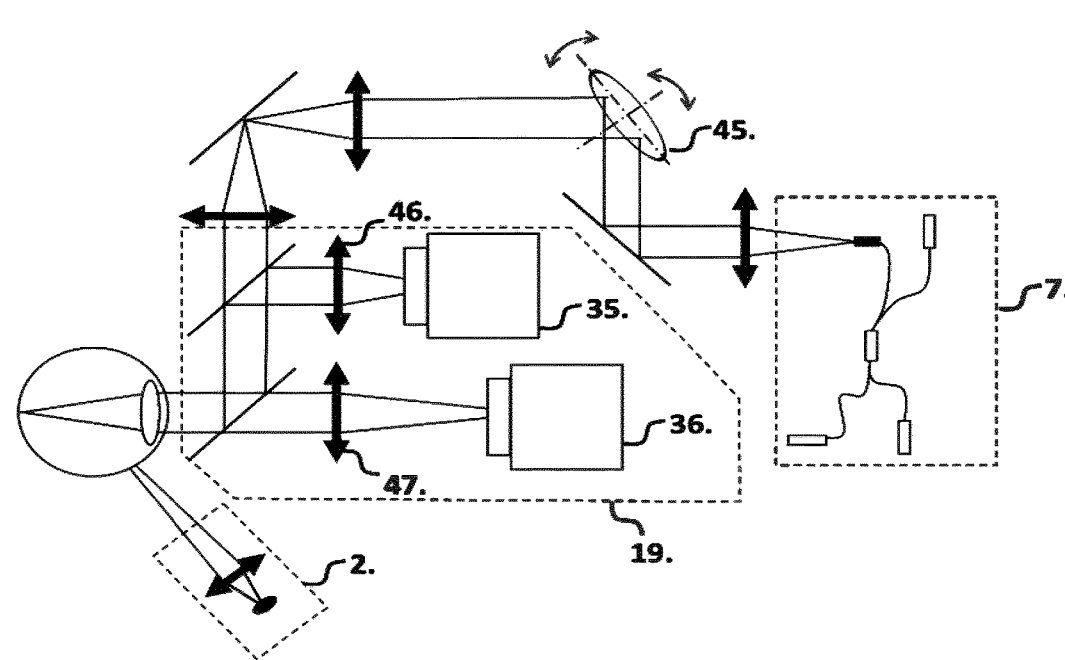

FIG: 5
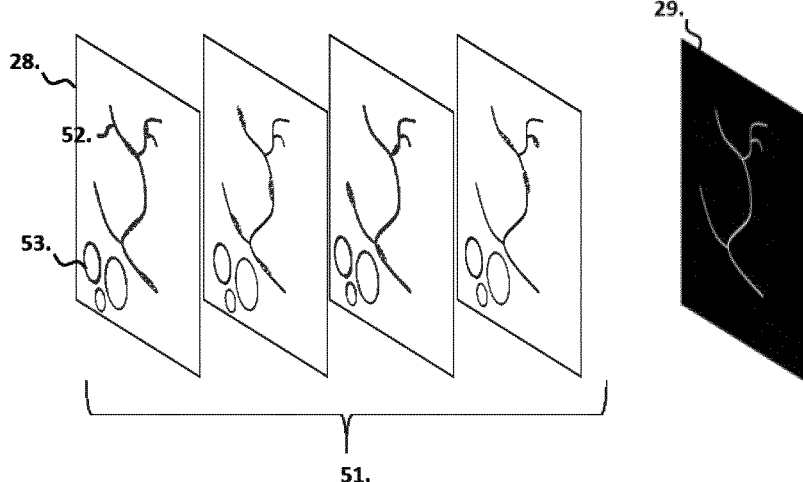
FIG: 6
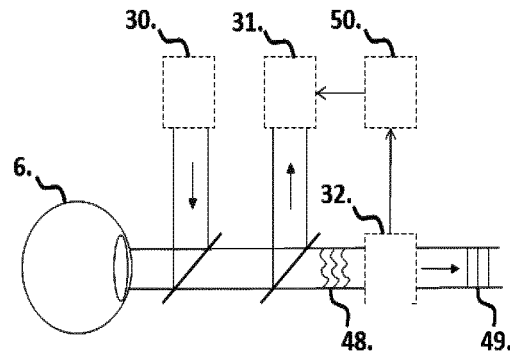

FIG: 7
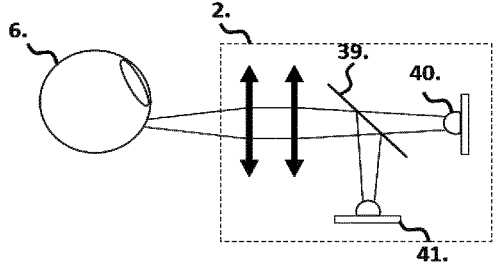
FIG: 8
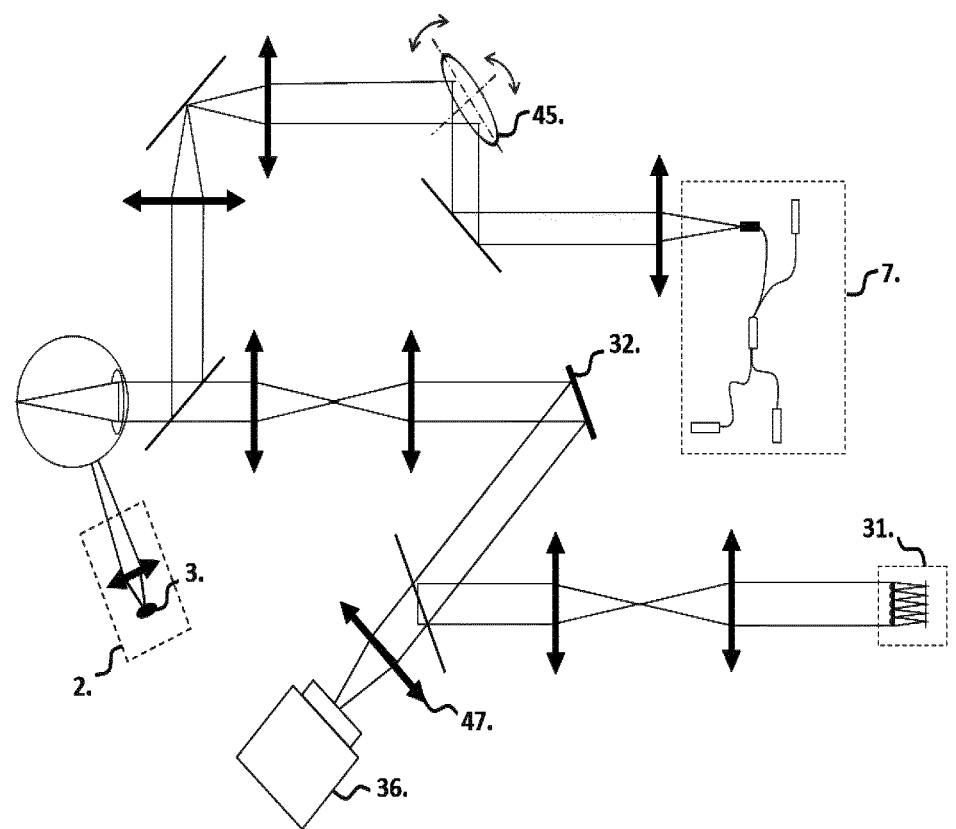

MULTI-MODAL RETINAL IMAGING PLATFORM

CROSS-REFERENCE TO RELATED APPLICATION(S)

This application is the U.S. national phase of International Application No. PCT/EP2021/057680 filed Mar. 25, 2021, which designated the U.S. and claims priority to EP 20166482.8 filed Mar. 27, 2020, the entire contents of each of which are hereby incorporated by reference.

TECHNICAL FIELD

The invention relates to an ophthalmic illumination and imaging system with an oblique transscleral illumination of an eye fundus with at least one physical point light source around the eye allowing for imaging (for instance dark field) combined with optical coherence tomography imaging.

BACKGROUND OF THE ART

Retinal diseases are the major cause of blindness in industrialized countries. For example, an estimated 196 million people will be affected by age-related macular degeneration in 2020. Although tremendous effort is being made to develop novel therapeutic strategies to rescue retinal neurons and the retinal pigment epithelium (RPE), optimal means for evaluating the effects of such treatments are still missing. The instruments used in eye clinics for routine eye fundus examination are not able to observe the minute changes in cell morphology that are present during early stages of the disease degenerative process.

The retina is an intricate and complex tissue composed of many layers. Individual cell imaging is very challenging for many reasons, including ocular aberration reducing the lateral resolution, as well as eye-motion artefacts and a lack of contrast of transparent cells.

Another limitation is that most of the light entering the pupil is either absorbed or reflected at the interface of photoreceptor segments, overwhelming the weak signal backscattered from the neuronal or RPE cells. The photoreceptor signal is maximum for an illumination beam entering the center of the eye pupil and decreases sharply when entering at its edge. This angular-dependent reflection of the retina is commonly termed the optical Stiles-Crawford effect (SCE).

The light reflected by photoreceptors renders their observation possible using adaptive optics (AO) to correct ocular aberrations combined with flood illumination optical coherence tomography (OCT) or scanning laser ophthalmoscopy (SLO). In recent works, optical methods to observe the neuroretina and RPE cells were proposed that use AO-SLO with offset aperture, split detector, dark-field, auto fluorescence or AO-OCT.

Despite the high quality results obtained, these methods suffer from a very small field of view (FOV), a lack of image clarity, safety concerns or an acquisition time that is too long for clinical use.

Applicant described in WO/2017/195163 Al (ECOLE POLYTECHNIQUE FEDERALE DE LAUSANNE (EPFL) [CH]), a method for imaging a tissue of an eye, the method including the steps of providing oblique illumination to the eye by a plurality of light emitting areas of a light delivery device, the plurality of light emitting areas being independently controllable and arranged to direct light towards at least one of a retina and an iris of the eye, causing an output beam from light backscattered from the at least one of the retina and the iris by the oblique illumination, capturing the output beam with an imaging system to provide a sequence of images of a fundus of the eye, and retrieving a phase and absorption contrast image from the sequence of images of the fundus, wherein the sequence of images of the fundus of the step of capturing is obtained by sequentially turning on one or more of the plurality of light emitting areas at a time in the step of providing the oblique illumination. In other words, the method for transscleral illumination, allowing for dark field and phase gradient techniques by using the scattering properties of the fundus. Transscleral oblique flood illumination increases the contrast of many biological structures composing the retina layers and, coupled with adaptive optics high-resolution imaging, enables the observation of cells which play a key role in the diseases-related degenerative process. Obtaining a cellular-level high-resolution image enables a new view of the structure of the retina resulting in a better understanding of the degenerative retinal disease processes.

The in vivo observation of the human retina at the cellular level is crucial to detect lesions before irreversible visual loss occurs, to follow the time course of retinal diseases and to evaluate and monitor the early effects of treatments. Despite the phenomenal advances in optical coherence tomography (OCT) and adaptive optics systems, in vivo imaging of several retinal cells is still elusive.

Laforest T. et al. "Transscleral Optical Phase Imaging of the Human Retina—TOPI" https://arxiv.org/abs/1905.06877 disclosed a transscleral optical phase imaging (TOPI), which allows to image retinal cells with high contrast, high resolution, and within an acquisition time suitable for clinical use. TOPI relies on high-angle oblique illumination of the retina, combined with adaptive optics, to enhance the phase contrast of transparent cells.

Transscleral optical phase imaging (TOPI) provides cellular-resolution label-free high contrast images of the retinal layers over a large FOV without the drawback of a long exposure time. This method is based on transscleral flood illumination of the retina, which greatly increases the signal-to-noise ratio (SNR) of many retina structures as compared to transpupillary illumination. The light transmitted through the sclera creates an oblique illumination of the posterior retina; this is then imaged using a transpupillary AO full-field camera system.

It was demonstrated in healthy volunteers without pupil dilation, that TOPI provides images of RPE cells and other retinal structures and enables cell quantification. Also demonstrated was the potential of this technology on ex vivo samples using an experimental phase microscope with parameters similar to those of the in vivo apparatus. It was shown that label-free phase images of the cells in thick retina samples match the quality of confocal fluorescence microscopy.

The method described in WO/2018/197288 A1 (IMAGINE EYES [FR]), is a multi-scale device, with several illumination modules coupled with a scanning system. The scanning system is made by either a SLO or OCT methods with adaptive optics. The multiscale allows the localization of the high-resolution image on the eye fundus but the transpupil illumination modules does not allow the observation of retinal pigment epithelium cells playing a key role in degenerative retinal diseases.

Fundus camera systems have been developed using transscleral illumination or transpalpebral illumination. WO/2017/151921 Al (BIOLIGHT ENG LLC [US]) describes a wide field transscleral or transpalpebral system using different apparatus for the light projection system and shapes and the sclera/skin tissues. WO/2004/091362 A2 (MEDIBELL MEDICAL VISION TECHNOLOGIES LTD. [IL]) discloses a fundus imaging system by projection of a beam on the sclera. Another device using transscleral illumination for imaging the choroid is disclosed in US2015/055094 A1 (ANNIDIS HEALTH SYSTEMS CORP [CA]).

Finally in 2017, Lingenfelder et al. presented a transscleral illumination system using LEDs Transscleral LED illumination pen', Biomed. Eng. Lett. 7, 2017. All these methods are aimed to provide images of the eye fundus over a large field-of-view to show the large structures such as blood vessels, but their purpose is not to look inside the tissue at the microscopic scale and cellular-level.

None of these methods are using adaptive optics to correct the ocular aberration and reach the diffraction limit of resolution. Consequently, none of these methods are able to provide the observation of the individual cells composing the retina tissues.

SUMMARY OF THE INVENTION

It is believed that none of the systems of the prior art provides a system using an oblique transscleral/transpalpebral illumination to provide simultaneously an en-face cellular level high-resolution image of a retina and an optical coherence tomography (OCT) system to visualize the in-depth cross-sectional area of the imaged retina.

A drawback of cellular level high-resolution imaging is the difficulty to choose and locate the depth of the imaging zone within the multi-layered retina tissue. OCT is a method specifically developed to observe in depth the structure of a tissue. Combing an OCT system to a cellular level high-resolution image produced by oblique flood illumination enables the precise localization of the cellular level high-resolution image and allows medical doctors to choose which layer of cells they are imaging. As with the addition of a large field-of-view fundus visualisation, having also the cross-sectional in-depth view of the retina enables the understanding of what part of the eye fundus tissue is imaged on the cellular-level high-resolution image. The horizontal or lateral location is provided by the large-field-of-view, and the vertical or in depth location by OCT. Depending on the speed of its attached scanning system, the OCT system could simultaneously be used both for the large field-of-view image and for the cross-section image.

Advantageously, according to the present invention, optical coherence tomography depth-related signal provides depth information of the front facing, in other words en-face, images within the eye fundus tissues. The depth-related signal contains information about the in-depth biological structure of the eye fundus tissues. The front facing images are showing a front facing imaging plane inside the same tissues, but the precise depth of this imaging plane is not easy to locate on its own. The optical imaging system producing the front facing images has a focus system able to change the depth of the imaging plane. For instance, with a known calibration of the OCT system and the front facing imaging focus system, the depth of the front facing imaging plane can be inferred from the OCT depth-related signal.

In accordance with the invention, the depth-related signal is processed to provide a direct feedback to adjust the depth of imaging of the front facing images.

For instance, the invention can further comprise a calibration step to match the depth scale of the depth-related signal with the one of the transscleral signal.

In accordance with the present invention, the depth related signal from the OCT system is used as a direct feedback on the depth of imaging of imaging system.

The feedback is used to perform depth control of the imaging depth. The control can be performed as an automatic—closed loop—depth control of the imaging depth or as an open loop user-control of the imaging depth.

The control of the imaging depth of the optical imaging system is therefore directly linked to the feedback signal of the OCT system. This allows to obtain «en face» oblique illumination images at a given depth of interest. This is particularly useful for pathological retina which have damages on the layered structure.—obtain a stack of «en face» images directly correlated with the precise depth of the OCT system.

locate and correlate precisely the "en face" images with the morphology of the different retina layers obtained with the OCT system.

correctly identify the type of cells or tissue structures present in the "en face" image.

create better quality "en face" images by knowing from the OCT system the correct optical defocus in the imaging system that is link to the specific retina layer we want to image.

Thus, one of the objects of the present invention is to provide an ophthalmic illumination system and method for transscleral illumination combined with an optical coherence tomography system probing the eye fundus through the eye pupil.

In particular, the invention provides for an ophthalmic illumination system comprising the combination of:

a transscleral light-delivering system with one or multiple light sources emitting light towards the sclera or surrounding skin of the intended eye to measure, providing transscleral oblique illumination of the eye fundus (1); and an optical coherence tomography (OCT) system directed toward the pupil of the intended eye to measure, comprising an OCT light source, a reference arm, a sample arm and a detection arm.

Another object of the invention is an ophthalmic illumination and imaging system comprising, preferably the combination of:

an oblique light-delivering system with one or multiple light sources emitting transscleral or transpalpebral illumination light towards respectively the sclera or surrounding skin of an intended eye to measure providing oblique illumination of the eye fundus; and an optical coherence tomography system directed toward the pupil of the intended eye to measure, comprising an OCT light source, a reference arm, a sample arm and a detection arm characterized in that the system further comprises an optical imaging system collecting the oblique illumination light scattered by the eye fundus, and making one or multiple front facing images of the eye fundus, the optical imaging system further comprising a focus system configured to adjust the depth of the imaging plane of the imaging optical system depending on a depth related signal provided by the OCT system.

Another object of the invention is to provide an ophthalmic illumination and imaging device, wherein a transscleral light-delivering system is combined with an OCT system, said ophthalmic illumination and imaging device comprises:

a scanning system to scan the eye fundus with said OCT system, a system for aberration correction including a probing light source, a wavefront sensor and a wavefront corrector, a system for high resolution transscleral anatomy or angiography imaging with a high-resolution camera, a system for large field of view transscleral anatomy or angiography imaging with a large field of view camera, and a system for transpupil anatomy or angiography imaging including a transpupil flood illumination source and a high-resolution camera.

An advantage of the present invention is to provide a cellular-level, high-resolution imaging of the eye fundus tissues using the scattered transscleral light and active or passive correction of the optical aberrations of the eye, and to locate the depth of imaging thanks to the OCT system. The passive aberration correction is, but not limited to custom lens or mirror. The active aberration correction is, but not limited to deformable mirror, tuneable lens or liquid crystal phase modulator.

Another object or advantage of the present invention is to provide a direct feedback on the depth of imaging of the transscleral high-resolution imaging system with the signal from the optical coherence tomography system. The feedback is used preferably to perform an automatic—closed loop—depth control of the imaging depth or to perform an open loop user-control of the imaging depth. The control of the high-resolution imaging depth is therefore directly linked to the feedback signal of the OCT system.

Other objects and advantages of the invention will become apparent to those skilled in the art from a review of the ensuing detailed description, which proceeds with reference to the following illustrative drawings, and the attendant claims.

BRIEF DESCRIPTION OF THE DRAWINGS

Further particular advantages and features of the invention will become more apparent from the following non-limitative description of at least one embodiment of the invention which will refer to the accompanying drawings, wherein FIG. 1: illustrates the combination of an OCT system with a transscleral illumination of the eye by means of a light delivering system.

FIG. 2: illustrates the principle of transscleral illumination of an eye fundus.

FIG. 3: illustrates the principle of transpalpebral illumination of an eye fundus.

FIG. 4: shows the system of FIG. 1 implemented with a front facing optical imaging system providing front facing images of the eye fundus thanks to two different light detectors (cameras).

FIG. 5: illustrates the principle of the extraction of blood vessels information from a sequence of anatomy images and produces angiography image.

FIG. 6: is a scheme of the adaptive optics principle composed of a transpupil probing light source, a wavefront sensor and a wavefront corrector.

FIG. 7: illustrates an apparatus of the ophthalmic illumination system able to produce a multi-wavelength transscleral illumination.

FIG. 8: illustrates an apparatus of the system for implementing the imaging modes described in FIG. 1, where the large field-of-view retina image is produced by a scanning (point-by-point) imaging system.

DETAILED DESCRIPTION OF THE INVENTION

Figure 9:
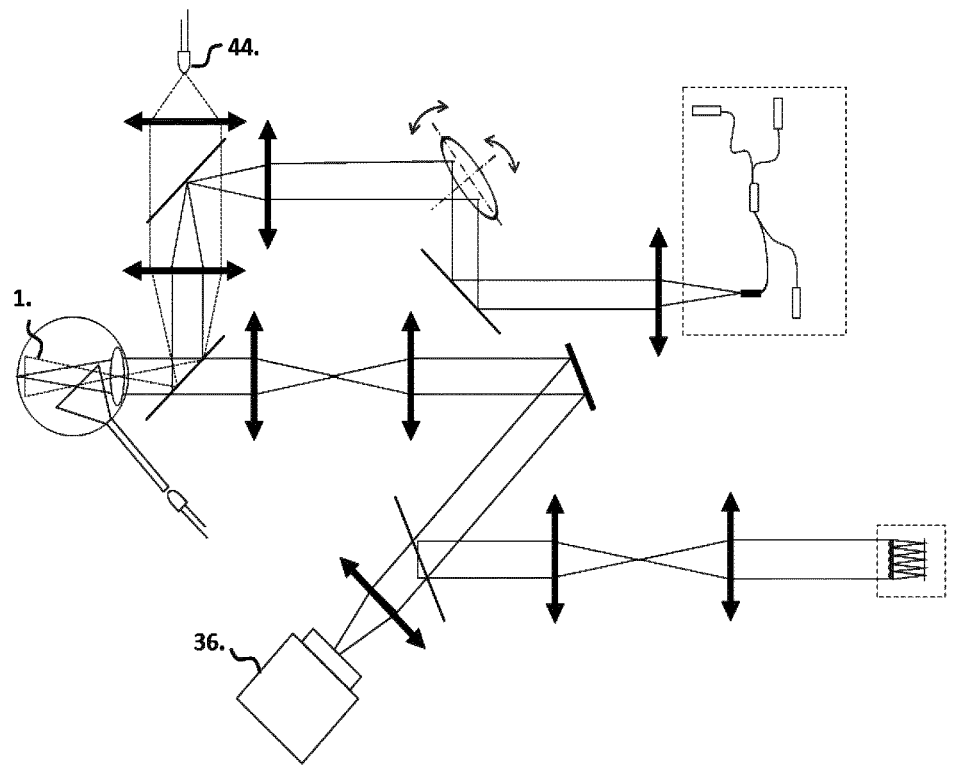
FIG. 9: illustrates an apparatus of the system for implementing the imaging modes described in FIG. 2, where a transpupil flood illumination modality is added to the main transscleral illumination.

Although methods and materials similar or equivalent to those described herein can be used in the practice or testing of the present invention, suitable methods and materials are described below. All publications, patent applications, patents, and other references mentioned herein are incorporated by reference in their entirety. The publications and applications discussed herein are provided solely for their disclosure prior to the filing date of the present application. Nothing herein is to be construed as an admission that the present invention is not entitled to antedate such publication by virtue of prior invention. In addition, the materials, methods, and examples are illustrative only and are not intended to be limiting.

In the case of conflict, the present specification, including definitions, will control.

Unless defined otherwise, all technical and scientific terms used herein have the same meaning as is commonly understood by one of skill in art to which the subject matter herein belongs. As used herein, the following definitions are supplied in order to facilitate the understanding of the present invention.

The term "comprise" is generally used in the sense of include, that is to say permitting the presence of one or more features or components.

As used in the specification and claims, the singular forms "a", "an" and "the" include plural references unless the context clearly dictates otherwise.

As used herein the terms "subject" or "patient" are well-recognized in the art, and, are used interchangeably herein to refer to a mammal, and, most preferably, a human. In some embodiments, the subject can be a normal subject. The term does not denote a particular age or sex. Thus, adult and newborn subjects, whether male or female, are intended to be covered.

Optical coherence tomography (OCT) is an imaging technique that uses low-coherence light to capture micrometer-resolution, one-, two- and three-dimensional images from within optical scattering media (e.g., biological tissue). It is used for medical imaging and industrial non—destructive testing (NDT). Optical coherence tomography is based on low-coherence interferometry, typically employing near-infrared light. The use of relatively long wavelength light allows it to penetrate into the scattering medium. Confocal microscopy, another optical technique, typically penetrates less deeply into the sample but with higher resolution.

Scattering is the process in which electromagnetic radiation (e.g. light) or particles are deflected or diffused as a result of their interaction with the matter.

Backscatter (or backscattering) is the reflection of electromagnetic radiation, particles, or signals back to the direction from which they came. It is usually a diffuse reflection due to scattering, as opposed to specular reflection as from a mirror, although specular backscattering can occur at normal incidence with a surface.

The "sclera", also known as the white of the eye, is the opaque, fibrous, protective, outer layer of the human eye containing mainly collagen and some elastic fiber. The sclera is a connective tissue made mostly of white collagen fibers. It underlies the choroid posteriorly and continues anteriorly where it becomes transparent over the iris and pupil and is referred to as the cornea.

The "eye fundus" or fundus of the eye is the interior surface of the eye opposite the lens and includes the retina, optic disc, macula, fovea, and posterior pole. The fundus can be examined by ophthalmoscopy and/or fundus photography.

The term "transscleral" means across the sclera, or white, of the eye.

The term "transpalpebral" means through the eyelid or the skin surrounding the eye and through the subsequent sclera.

A first object of the invention is to provide an ophthalmic illumination system, the system comprising the combination of:

a transscleral light-delivering system (2) with one or multiple light sources emitting light towards the sclera (4) or surrounding skin (5) of the intended eye to measure, providing transscleral oblique illumination of the eye fundus (1); and an optical coherence tomography (OCT) system (7) directed toward the pupil (8) of the intended eye (6) to measure, comprising an OCT light source (9), a reference arm (10), a sample arm (11), an optical beam splitter (12) and a detection arm (14).

Preferably, the light-delivering system (2) is not in contact with the skin surrounding the intended eye to measure or the sclera.

Advantageously, the optical coherence tomography system is producing a depth-related signal(15) of the biological structure of the eye fundus tissues and making one- (16), two- (17) or three-dimensional (18) OCT images of said eye fundus (1).

Preferably, the invention further comprises an optical imaging system (17) collecting the transscleral oblique illumination light scattered by the eye fundus (1), and making one or multiple front facing (en-face) images (51) of the eye fundus (1) on one or multiple light sensitive detectors or cameras (35, 36).

According to one embodiment, a sequence of front facing images (51) is analysed and processed to extract time-correlated information and enhance the contrast of time-changing biological bodies such as blood vessels (52).

According to the invention, said optical coherence tomography system depth-related signal (15) provides depth information of the front facing images (51) within the eye fundus tissues.

According to one embodiment, said optical coherence tomography system depth-related signal (15) is processed to provide a real-time closed-loop feedback (56) to control the depth of imaging of the front facing images (51).

According to another embodiment, said optical coherence tomography system depth-related signal (15) is processed to provide an open-loop control of the depth of imaging of the front facing images (51).

Advantageously, the ophthalmic illumination system of the invention further comprises a correction of the optical aberrations of the eye for at least one front-facing image (51).

According to one embodiment, the correction of the optical aberrations is performed through static optical elements or computational means.

According to another embodiment, the correction of the optical aberrations is performed in real-time with an adaptive optics closed-loop comprising a transpupil probing light source (30), a wavefront sensor (31) and a wavefront corrector (32) able to spatially shape the wavefront of the light making a front-facing image (51).

Preferably, the transpupil probing light source (30) is the same as the OCT light source (9).

According to yet another embodiment, the ophthalmic illumination system of the invention further comprises a transpupil flood illumination source (44) and an imaging system producing front-facing images (51) of the eye fundus (1) from the back-scattered light (23) derived from said transpupil flood illumination source (44).

Preferably, the light delivering system (2) providing transscleral oblique illumination of the eye fundus (1) has different wavelengths. Advantageously, said different wavelengths provide a functional information selected from the list comprising: blood flow oxygenation and retinal pigment epithelium cells' activity.

Another object of the invention is to provide an ophthalmic illumination and imaging device, wherein a transscleral light-delivering system (2) is combined with an OCT system (7) as described above, wherein said ophthalmic illumination and imaging device comprises:

a scanning system (45) to scan the eye fundus (1) with said OCT system (7), a system for aberration correction including a probing light source (30), a wavefront sensor (31) and a wavefront corrector (32), a system for high resolution transscleral anatomy or angiography imaging (28, 29) with a high-resolution camera (36), a system for large field of view transscleral anatomy or angiography imaging (26, 27) with a large field of view camera (35), and a system for transpupil anatomy or angiography imaging (24) including a transpupil flood illumination source (21) and a high-resolution camera (36).

The invention is further described in respect of various particular embodiments as follows:

The transscleral light-delivering system 2 (see FIG. 1), comprises at least one light source 3 emitting a light beam 59 toward an eye 6. The light beam reaches the surface of the sclera 4 or the skin surrounding the eye 5 and diffuses inside the tissues. A part is transmitted across the sclera 4 and full eye envelope 58, propagates inside the vitreous body 57, and illuminates the eye fundus obliquely 1. This illumination is called transscleral oblique illumination of the eye fundus.

Illumination is provided thanks to a single or a combination of light sources in the wavelength range of 400 nm to 1200 nm such as but not limited to: light emitting diode, super luminescent diode, quantum dot source, a lamp, a black body radiation source, and a laser source.

Light is delivered by placing the source in direct contact with the tissue (sclera or skin) or guided from the source to the tissue with a guiding material such as, but not limited to, water, polymer or glass, or propagating in air from the source to the illumination surface (cornea, sclera or skin). Light beam can be converging, diverging or collimated, depending on the chosen illumination technique. Light can be but not limited to linearly polarized, circularly polarized, non-polarized (meaning that does not presents any known preferential polarization), and a mixture of different polarizations.

In Fourier domain, oblique illumination with a plane wave is equivalent to a shift towards higher spatial frequencies. In addition, shining light on the fundus with higher angles will also produce a more oblique back illumination, providing higher contrast.

Advantageously, the optical coherence tomography system 7 is producing a depth-related signal (15) of the biological structure of the eye fundus tissues and making one-, two- or three-dimensional depth-related signal of the eye fundus 1. The OCT light source (9) is emitting light that is split into the reference arm 10 and the sample arm 11. The light beam of the sample arm 11 is propagating up to the eye fundus 1 tissues, where a part is reflected and goes back to the OCT system detection arm 14. The light beam of the reference arm 10 is reflected on a mirror surface 33 and also goes back to the detection arm 14. The two light beams reflected from the sample arm 11 and reference arm 10 are interfering in the detection arm 14, and the intensity of this interference is measured by a light detector 13 at the end of the detection arm. The detector 13 is, but is not limited to, a spectrometer 38 that comprises a diffraction grating 37 and a line-array detector 38 in case of spectral domain OCT, or a photodiode for swept-source OCT. The electric signal coming out of the detector is the depth-related signal 15 of the biological structure of the eye fundus. Depending on the configuration of the scanning system 45, the depth-related signal 15 is further used by a computer to produce one-, two- or three-dimensional OCT images of the eye fundus. No scanning system enables the computation of one-dimensional 16 depth-related signal showing a depth-line inside the eye fundus tissues. A single axis scanning system enables the computation of two-dimensional 17 depth-related signal of the eye fundus showing a cross-section inside the eye fundus tissues. A two-axis scanning system, or two single-axis scanning system, enables the computation of three-dimensional 18 depth-related signal of the eye fundus showing a volume inside the eye fundus tissues. The scanning system are consecutively tilted to direct the light beam of the sample arm 11 at different point inside the eye fundus in order to record the depth-related signal 15 over an area or volume of the tissues.

Preferably, the invention further comprises an optical imaging system 19, illustrated in FIG. 4, collecting the transscleral oblique illumination light scattered by the eye fundus 1, and making one or multiple front facing (en-face) images 51 of the eye fundus on one or multiple light sensitive detectors (cameras) (35, 36). The optical imaging system 19 comprises optical lenses and mirrors to conjugate the eye fundus plane with the detector plane of the cameras. The cameras are thus able to capture the light scattered by the eye fundus and to produce images of the eye fundus. By playing on the focal length of the optical lenses, images with different magnification of the eye fundus can be produced on different cameras.

In one embodiment, according to FIG. 4, a high-resolution front facing image is produced on a camera 36 thanks to a long focal length imaging lens 47. In the same embodiment, a large field-of-view front facing image is produced on a camera 35 thanks to a shorter focal length imaging lens 46.

According to one embodiment, as illustrated in FIG. 5, a sequence of front facing images 51 is analysed and processed to extract time-correlated information and enhance the contrast of time-changing biological bodies such as blood vessels.

According to FIG. 6, a sequence of front facing images of the eye fundus 51, containing retinal vessels 52 and other tissue structures static 53 over time. Since blood signal is changing over time, when computing the time correlation image 41, only the vessels image (angiography) is extracted from the image sequence.

Preferably, the light sources illuminating the sclera 4 have different wavelengths by means or two LEDs 40 and 41 (FIG. 7), which provide a functional information. Different wavelengths are used for the front facing images, and the images are processed in order to extract functional information of the retina such as, but not limited to, blood flow oxygenation or retinal pigment epithelium (RPE) cells health.

LEDs 40 and 41 have peak wavelengths of 810 nm and 890 nm allowing the differentiation of oxygenation of the vessels thanks to the different absorption curves of oxygenated haemoglobin versus non-oxygenated haemoglobin.

An implementation is shown according to FIG. 7 where two LEDs 40 and 41 having different peak wavelengths $\lambda 1$ and $\lambda 2$ are used to provide the two sources of transscleral illumination. They are combined thanks to the dichroic mirror 39 and illuminates the scleral of the eye 6 thanks to the transscleral light delivering system 2.

According to a particular embodiment of the invention, optical coherence tomography depth-related signal 15 provides depth information of the front facing images within the eye fundus tissues. As described above, the depth-related signal contains information about the in-depth biological structure of the eye fundus tissues. The front facing images are showing a front facing imaging plane inside the same tissues, but the precise depth of this imaging plane is not easy to locate on its own. The optical imaging system 19 producing the front facing images 26, 27, 28, 29 has a focus system able to change the depth of the imaging plane. With a known calibration of the OCT system 7 and the front facing imaging focus system, the depth of the front facing imaging plane can be inferred from the OCT depth-related signal 15.

According to another embodiment, the invention further comprises a correction of the optical aberrations of the eye for at least one front-facing image. The lateral resolution of imaging inside an eye is limited by its pupil size and by the optical aberrations of the eye. The lateral resolution of imaging is directly linked to the smallest element that is observable inside the eye fundus tissues. A better or higher lateral resolution means that a smaller element can be observed and that more details are visible inside the tissues. A way to increase this lateral resolution and to maximize the details visible in the tissue is to correct the aberrations of the eye by computational means or optical elements. If the aberrations are completely corrected, one reaches so called diffraction-limited imaging performance inside the eye (i.e. limited only by the diffraction of light due to the finite aperture size of the eye pupil).

Advantageously, the correction of the aberrations is performed by static optical elements. Static optical elements are, but not limited to, custom lens of mirror correcting for defocus, astigmatism, a badal system.

Alternatively, the correction of the aberrations is performed computationally on the recorded images with image processing techniques. Computational correction of the aberrations consists of, but is not limited to, using a measure of the aberrations of the eye and the optical imaging system and digitally modifying the image in order to account and correct for said aberrations.

Alternatively, the correction of the aberrations is performed in real-time by measurement of the aberrations, according to FIG. 6, with a transpupil probing light source 30 and a wavefront sensor 31, and wavefront corrector 32 able to spatially shape the collected light wavefront. This principle of correction of the aberration of the eye is usually referred as adaptive optics loop and consists on the following: The transpupil probing light source 30 is focused on the eye fundus. A fraction of the focused light is backscattered and illuminates the wavefront sensor 31 placed in a pupil conjugated plane 42. The wavefront sensor is preferably implemented as a Shack-Hartmann sensor. The wavefront sensor is placed in plane conjugated to the eye pupil plane. The image recorded on the wavefront sensor allows the measure of the light wavefront aberrations that are related to the aberrations of the eye. The control for the wavefront corrector 32 is computed and applied. The wavefront corrector is, but not limited to, a deformable mirror, a tunable lens, a liquid crystal modulator. The wavefront corrector is placed in a conjugated eye pupil plane in between the eye pupil 8 and the wavefront sensor 31. The change of shape of the wavefront corrector 32 will try to cancel the aberrations of the eye.

According to yet another embodiment, as shown in FIG. 9, the invention further comprises a transpupil flood illumination source 44 and an imaging system producing front-facing images of the eye fundus 1 through the back-scattered light from said illumination source.

In accordance with the invention, the depth-related signal 15 is processed to provide a direct feedback to adjust the depth of imaging of the front facing images.

Preferably, the transpupil probing light source 30 for aberrations measurement is the same as the OCT light source 9.

The invention further comprises a calibration step to match the depth scale of the depth-related signal 15 with the one of the transscleral signal.

The image acquisition process is different depending on the required imaging modality: dark field or phase/absorption. For dark field, imaging can be performed with just one illumination point without image processing. A wider field of view is obtained by stitching together images obtained for different imaging areas.

Transscleral illumination has two interesting properties that increase the low contrast of the retina observed with transpupil flood illumination. First, due to the SCE, almost no high-angle transscleral illumination light is coupled into the photoreceptors, allowing a large fraction of the light to reach the RPE layer. Second, no direct backscattered illumination light is collected by the imaging system because there is no overlap with the collection path located through the pupil. Thus, only the light multiply scattered by the different retina layers enters the optical system and reaches the camera, providing a dark-field imaging condition. The illumination angle is much larger than what is obtainable via illumination through the pupil, creating a non-uniform excitation of the retina spatial frequencies that enhances the contrast of transparent objects.

As described above, this invention concerns an ophthalmic illumination system and imaging device for transscleral illumination, cellular-level front facing high-resolution imaging, large field-of-view imaging and in-depth visualization of the eye fundus. The high-resolution image is provided thanks to transscleral illumination coupled with correction of optical aberrations of the eye and the in-depth visualization is provided by optical coherence tomography.

In a first embodiment, according to FIG. 1, the system comprises, but is not limited to, a transscleral light delivering system 2 with one or multiple emitting areas 3, that illuminate the sclera 4 without any contact, intended to illuminate in turn the eye fundus 1 obliquely, combined with an OCT system 7 comprising an OCT light source 9, an optical beam splitter 12, a reference arm 10, a sample arm 11 and a light detection arm 14 and providing a depth-related signal 15.

In another embodiment, according to FIG. 4, the system comprises, but is not limited to, a main retinal high resolution camera 36 imaging the retina with high-resolution, with a digital sampling smaller than 2 μm/pixel and a second large field of view retinal camera 35 imaging the retina over a larger field of view (typically more than 30°), with a digital sampling of 20 μm/pixel.

In addition, the main retinal camera optical path includes an adaptive optics loop in order to correct the aberrations of the eye. The adaptive optics loop comprises, but is not limited to, a wavefront sensing light source directed toward the pupil of the eye, a Shack-Hartmann wavefront sensor 31 measuring the back-scattered light coming from the eye fundus, and a deformable mirror 19. The wavefront sensor 31 measures in real time the eye optical aberrations and send the control feedback to the deformable mirror. The wavefront sensing source is, but not limited to, a laser source, a superluminescent diode 17 or a light emitting diode (LED). The transpupil probing light source 30 is divided in 2 arms (sample arm 11 and reference arm 10) for performing an interference. The signal back-scattered from the retina is separated in 2 parts; one fraction will be used for wavefront measurement 5, and the other fraction for measuring an interference with the reference arm 10.

In another embodiment, according to FIG. 4, the large field-of-view front facing image is produced by an OCT system 7 or another eye scanning system such as scanning laser ophthalmoscope (SLO). A two-axis rotating mirror 31, or a couple of single axis rotating mirror, permits the OCT or scanning system 45 to image the eye fundus tissue over a three-dimensional 18 depth-related signal 15.

In another embodiment, according to FIG. 9, a transpupil flood light source 44 is included in the system is order to provide a transpupil flood illumination of the eye fundus 1 over a large area 34. The transpupil light source 33 is, but not limited to, a LED. The light coming from this source and back-scattered by the eye fundus 1 is used to create high-resolution images in the photoreceptors cells on the main retinal camera 25. The photoreceptor cells are directional cells reflecting a portion of the light entering the eye pupil 8 and are therefore better observable when using transpupil illumination compared to transscleral illumination.

Figure 10:
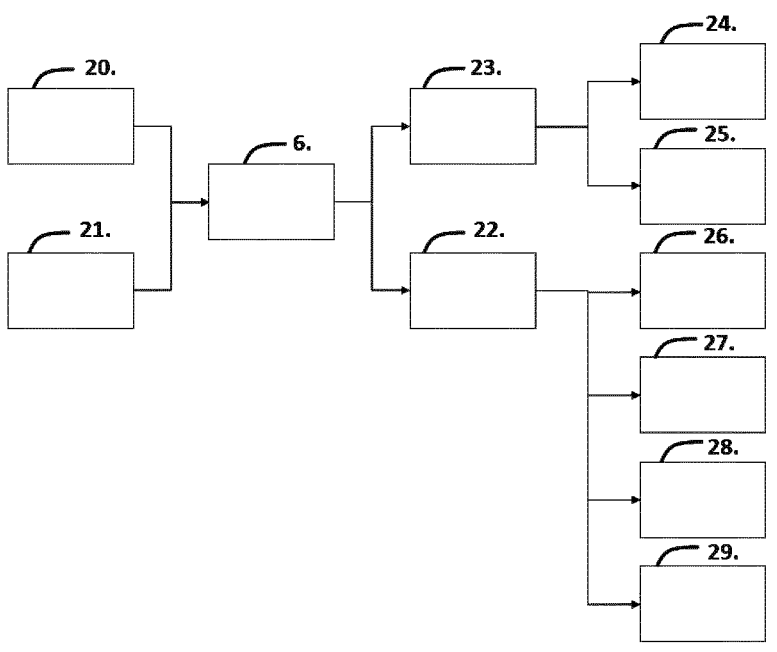
FIG. 10: shows the bloc diagram of the multi-modal imaging system, including transscleral high-resolution and large field of view, anatomical of angiography, transpupil high resolution, transpupil OCT.

According to FIG. 10, the light beam is directed either towards the sclera 4 or towards the pupil 8 of the eye 6. The back-scattered light from transpupil illumination 23 is collected to generate the following:

Transpupil retinal anatomy or angiography image 24

Optical coherence tomography retinal anatomy image 25

The multiply scattered light from transscleral illumination 22 is collected to generate the following:

Transscleral large field of view retinal anatomy image 26

Transscleral large field of view retinal angiography image 27

Transscleral high resolution retinal anatomy image 28

Transscleral high resolution retinal angiography image 29.

Figure 11:
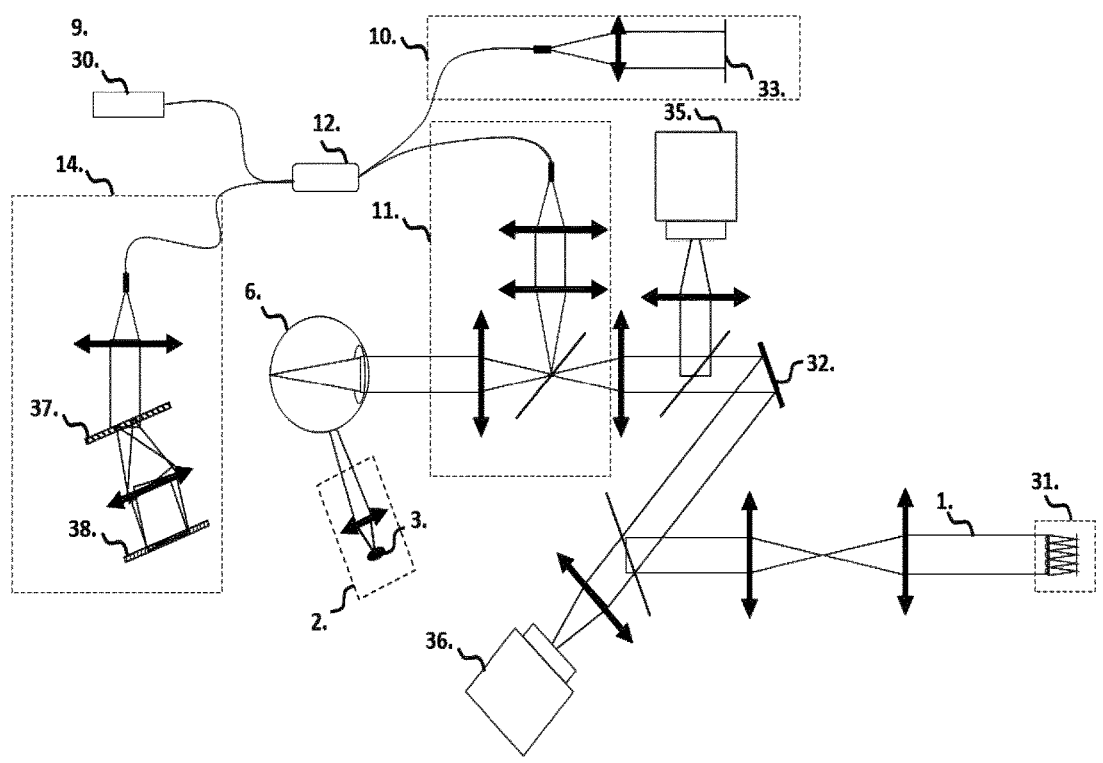
FIG. 11: shows an ophthalmic illumination and imaging device implementing the principles described in FIG. 1 to FIG. 10.

According to FIG. 11, after illuminating the eye 6, the light multiply scattered is collected by the ophthalmic illumination system. The light sources for OCT 9 or for wavefront transpupil probing 30 illuminates the eye 6 through the pupil 8. The transpupil probing light source for wavefront sensing 30 is recorded on the wavefront sensor 31 and gives a feedback to the wavefront corrector 32 in order to correct the ocular aberrations. The same transpupil probing light source for wavefront sensing 30 can be the same as the OCT source 9. The OCT system 7 consists in the reference arm 10 for its reference mirror 33. The fiber beam splitter 22 sends or collects the light from/to the eye 6. The beam splitter 23 also sends and collects the light from/to the OCT light source 17. The transscleral light source 16 illuminates the eye 6 and the multiply scattered light from transscleral illumination 22 is collected. The retina 14 is imaged on the large field of view camera 35 and the high-resolution camera 25. The sensors of the cameras are conjugated retina planes 43.

The following scheme is presented as embodiments:

The transscleral illumination system is coupled with an optical coherence tomography system 7.

According to FIGS. 1 and 4, the OCT system 7 is composed of a light beam towards the pupil 8, an OCT light source 13, a reference mirror 33, a fibre beam splitter 22, a diffraction grating 37, a multipixel light sensitive detector 27. After illuminating the retina, the light back-scattered from transpupil illumination 23 is collected and sent to the OCT system 7 thanks to the beam splitter 23 and recorded on the spectrometer 38 composed of the diffraction grating 37 and the light detector 13.

The high-resolution imaging system is collecting the transscleral illumination light going out of the pupil 8 and is correcting the optical aberrations of the eye with an adaptive optics system.

According to FIGS. 1 and 2, the beam towards the sclera 2 (transscleral light-delivering system) illuminates the eye fundus 1 after transmitting and diffusing inside the eye envelope tissue, and the light multiply-scattered from transscleral illumination 22 is collected by the imaging system and the retina is imaged on the high resolution camera 36 and large field of view camera 35. Optical aberrations are corrected thanks to the wavefront sensor 31 and wavefront corrector 32.

The adaptive optics system is composed by a probing source directed toward the eye pupil and reflecting on the eye fundus 1, a wavefront sensor 31 measuring the ocular aberration by analysing the probing source reflection and a wavefront corrector 32 correcting the ocular aberrations based on the wavefront sensor 31 measurements.

According to FIG. 2, the probing light source 18 is focused on the retina and the wavefront sensor 31 measures the ocular aberrations.

The wavefront probing source is used to measure the wavefront for one part and to produce an interference for the other part.

According to FIG. 2, the probing light source 18 is also used for the OCT light source 9. The splitting is performed either in intensity by mean of, but not limited to, beam splitter 23, dichroic mirror 39, or in wavelength.

The optical coherence tomography signal 7 is processed to deliver a feedback to the adaptive optics system in order to focus the high-resolution imaging system at the chosen depth.

In order to compute the feedback based on the depth-related signal 15, a calibration step is required to match the optical depth obtained with the OCT system 7 with the optical depth of the other imaging modalities. The calibration includes the positioning of the reference mirror 33, the adjustment imaging depth for a null defocus term applied of the wavefront corrector and the knowledge of the relation between the OCT depth of the other imaging modalities depth, which depends on the wavelength of the two.

Figure 12:
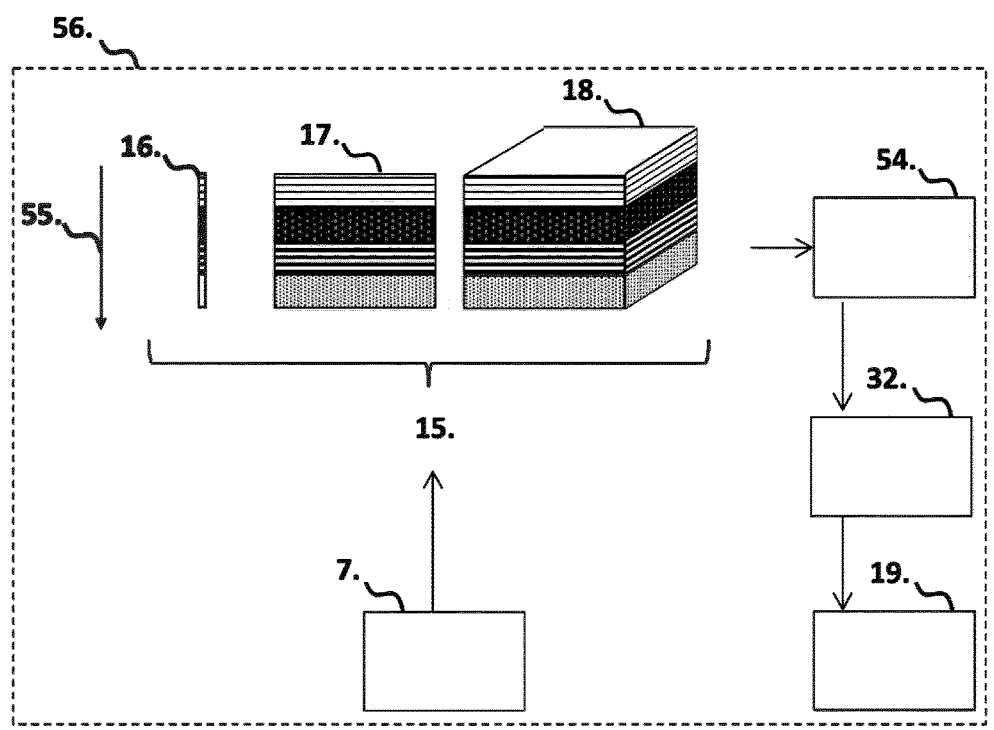
FIG. 12: illustrates the closed-loop depth control based on the depth-related signal obtained from the OCT system.
Figure 13:
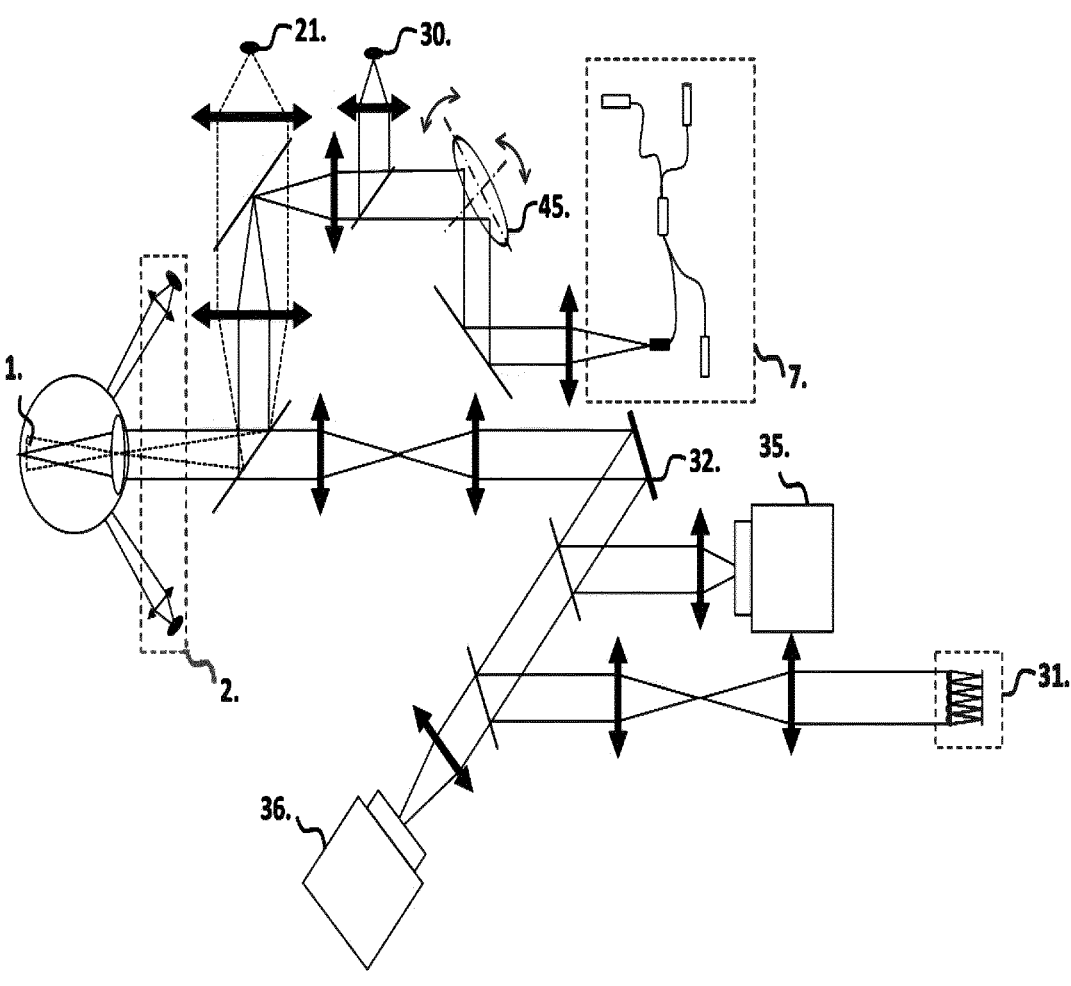
FIG. 13: shows the ophthalmic illumination and imaging device implementing the combination of many systems described in the present invention.

According to FIG. 12, the depth-related signal 15 from the spectrometer 38 is analysed to adapt the wavefront corrector 32 and focus on the desired retinal layer.

The depth-related signal 7 is obtained, but not limited to, thanks to a Fourier domain setup coupled with the wavefront probing source 18.

The transscleral-based images are processed with, but not limited to, time correlation method, to extract the functional image of the blood flow.

According to FIG. 11, the depth-related signal 15 is obtained thanks to an OCT system 7 implemented as a full field OCT, using the transpupil flood illumination source 44.

According to FIG. 10, the beam towards the sclera 2 is used to provide:

a transscleral Large field of view retinal anatomy image 26 a transscleral Large field of view retinal angiography image 27 a transscleral high resolution retinal anatomy image 28 a transscleral high resolution retinal angiography image 29.

Those skilled in the art will appreciate that the invention described herein is susceptible to variations and modifications other than those specifically described. It is to be understood that the invention includes all such variations and modifications without departing from the spirit or essential characteristics thereof. The invention also includes all of the steps, features, compositions and compounds referred to or indicated in this specification, individually or collectively, and any and all combinations or any two or more of said steps or features. The present disclosure is therefore to be considered as in all aspects illustrated and not restrictive, the scope of the invention being indicated by the appended Claims, and all changes which come within the meaning and range of equivalency are intended to be embraced therein.

Various references are cited throughout this specification, each of which is incorporated herein by reference in its entirety.

| REFERENCE NUMBERS | |
|---|---|
| 1 | eye fundus |
| 2 | transscleral light-delivering system |
| 3 | light source (transscleral) |
| 4 | sclera |
| 5 | skin surrounding the eye |
| 6 | eye |
| 7 | optical coherence tomography (OCT) system |
| 8 | pupil |
| 9 | OCT light source |
| 10 | Reference arm |
| 11 | Sample arm |
| 12 | Optical beam splitter |
| 13 | Light detector |

-continued

REFERENCE NUMBERS

| 14 | Detection arm |
|---|---|
| 15 | Depth-related signal |
| 16 | 1D image |
| 17 | 2D image |
| 18 | 3D image |
| 19 | optical imaging system |
| 20 | Transscleral illumination |
| 21 | Transpupil illumination |
| 22 | Multiply-scattered light from transscleral illumination |
| 23 | Back-scattered light from transpupil illumination |
| 24 | Transpupil retinal anatomy or angiography imaging |
| 24 | Optical coherence tomography retinal anatomy imaging |
| 26 | Transscleral large field of view retinal anatomy imaging |
| 27 | Transscleral large field of view retinal angiography imaging |
| 28 | Transscleral high resolution retinal anatomy imaging |
| 29 | Transscleral high resolution retinal angiography imaging |
| 30 | Transpupil probing light source |
| 31 | Wavefront sensor |
| 32 | Wavefront corrector |
| 33 | Reference mirror |
| 34 | Optical beam splitter |
| 35 | Large field of view camera |
| 36 | High resolution camera |
| 37 | Diffraction grating |
| 38 | Spectrometer |
| 39 | Dichroic mirror separating λ1 and λ2 |
| 40 | LED with peak wavelength λ1 |
| 41 | LED with peak wavelength λ2 |
| 42 | Conjugated pupil plane |
| 43 | Conjugated retina plane |
| 44 | Transpupil flood illumination source |
| 45 | scanning system |
| 46 | large field of view imaging lens |
| 47 | high resolution imaging lens |
| 48 | Aberrated wavefront |
| 49 | Corrected wavefront |
| 50 | Wavefront computation |
| 51 | One or multiple front facing images |
| 52 | blood vessels |
| 53 | static structures |
| 54 | depth control calculation |
| 55 | depth axis |
| 56 | closed loop depth control |
| 57 | Vitreous body |
| 58 | Eye envelope |
| 59 | Light beam emitted by the light delivering system |

The invention claimed is:

1. An ophthalmic illumination system, comprising:
an oblique light-delivering system having one or multiple light sources emitting transscleral or transpalpebral illumination light towards respectively the sclera or surrounding skin of an intended eye to measure providing oblique illumination of the eye fundus; and
an optical coherence tomography (OCT) system directed toward the pupil of the intended eye to measure, comprising an OCT light source, a reference arm, a sample arm and a detection arm,
wherein the system further comprises an optical imaging system configured to collect the oblique illumination light scattered by the eye fundus, and make one or multiple front facing, namely en-face, images of the eye fundus, and
the optical imaging system further comprises a focus system configured to adjust the depth of the imaging plane of the optical imaging system depending on a depth related signal provided by the OCT system.

2. The system according to claim 1, wherein the optical coherence tomography system is further configured to make one-, two- or three-dimensional OCT images of said eye fundus.

3. The system according to 1, wherein the optical imaging system further comprises one or more light sensitive detectors or cameras to provide the front facing images of the eye fundus.

4. The system of claim 3, wherein a sequence of the front facing images is analysed and processed to extract time-correlated information and enhance the contrast of time-changing biological bodies such as blood vessels.

5. The system according to claim 1, wherein the depth-related signal provides depth information of the front facing images within the eye fundus tissues.

6. The system of claim 5, wherein the depth-related signal is processed to provide a real-time closed-loop feedback to control the depth of imaging of said front facing images.

7. The system according to claim 5, wherein the depth-related signal is processed to provide an open-loop control of the depth of imaging of the front facing images.

8. The system according to claim 3, further comprising correction means for correcting the optical aberrations of the eye for at least one of the front-facing images.

9. The system according to claim 8, wherein the correction means are chosen among static optical elements or computational means.

10. The system according to claim 8, wherein the correction of the optical aberrations is performed in real-time with an adaptive optics closed-loop comprising a transpupil probing light source, a wavefront sensor and a wavefront corrector able to spatially shape the wavefront of the light making a front-facing image.

11. The system of claim 10, wherein the transpupil probing light source is the same as the OCT light source.

12. The system according to claim 1, further comprising a transpupil flood illumination source and an imaging system producing front-facing images of the eye fundus from the back-scattered light derived from the transpupil flood illumination source.

13. The system according to claim 1, wherein the transscleral light delivering system providing the transscleral oblique illumination of the eye fundus has different wavelengths.

14. The system of claim 13, wherein the different wavelengths provide a functional information selected from the list comprising: blood flow oxygenation and retinal pigment epithelium cells' activity.

15. An ophthalmic illumination and imaging device, wherein a transscleral light-delivering system is combined with an OCT system according to claim 1, and the ophthalmic illumination and imaging device comprises:
a scanning system to scan the eye fundus with said OCT system;
a system for aberration correction including a probing light source, a wavefront sensor and a wavefront corrector;
a system for high resolution transscleral anatomy or angiography imaging with a high-resolution camera;
a system for large field of view transscleral anatomy or angiography imaging with a large field of view camera; and
a system for transpupil anatomy or angiography imaging including a transpupil flood illumination source and a high-resolution camera.

* * * * *